United States Patent
Bergman et al.

(10) Patent No.: US 8,974,749 B2
(45) Date of Patent: Mar. 10, 2015

(54) ASSAY DEVICE AND METHOD

(75) Inventors: David Bergman, Knivsta (SE); Ib Mendel-Hartvig, Uppsala (SE); Annika Lindström, Uppsala (SE)

(73) Assignee: Johnson & Johnson AB (SE)

( * ) Notice: Subject to any disclaimer, the term of this patent is extended or adjusted under 35 U.S.C. 154(b) by 1117 days.

(21) Appl. No.: 12/484,110

(22) Filed: Jun. 12, 2009

(65) Prior Publication Data

US 2009/0311805 A1 Dec. 17, 2009

Related U.S. Application Data (60) Provisional application No. 61/061,983, filed on Jun. 16, 2008.

(51) Int. Cl.
*B01L 3/00* (2006.01)
*G01N 33/558* (2006.01)

(52) U.S. Cl.
CPC ........ *G01N 33/558* (2013.01); *B01L 3/502746* (2013.01)
USPC ........... 422/507; 422/502; 422/503; 422/504; 436/518; 436/524

(58) Field of Classification Search
CPC ................................................ B01L 3/502746
USPC ........... 422/507, 502, 503, 504; 436/518, 524
See application file for complete search history.

(56) References Cited

U.S. PATENT DOCUMENTS

| 6,271,040 B1 | 8/2001 | Buechler |
| 6,762,059 B2 * | 7/2004 | Chan et al. .................... 436/164 |
| 6,767,510 B1 * | 7/2004 | Buechler ........................ 422/412 |
| 7,586,091 B2 * | 9/2009 | Takahashi et al. ............ 250/288 |
| 8,025,854 B2 * | 9/2011 | Ohman et al. ................. 422/507 |
| 2005/0026346 A1 | 2/2005 | Blankenstein et al. |
| 2005/0042766 A1 * | 2/2005 | Ohman et al. ................. 436/174 |

(Continued)

FOREIGN PATENT DOCUMENTS

| CN | 1597119 A | 3/2005 |
| EP | 1120164 A2 | 8/2001 |

(Continued)

OTHER PUBLICATIONS

Chinese Office Action for CN Application No. 200910149789.6; mailed May 11, 2012; 11 pages.

*Primary Examiner* — Melanie Y Brown
(74) *Attorney, Agent, or Firm* — Hiscock & Barclay, LLP (57) ABSTRACT

There is disclosed an analysis device for the analysis of a liquid sample, said device comprising a substrate, said substrate at least partly having projections substantially vertical to the surface of said substrate, and having a height (H1), diameter (D1) and center-to-center distance (x1, y1) such, that lateral capillary flow of said liquid sample is achieved, wherein that said substrate comprises at least one substrate zone comprising projections substantially vertical to the surface of said substrate, and having a height (H2), diameter (D2) and center-to-center distance (x2, y2), such, that lateral capillary flow of said liquid sample is achieved and wherein at least one substance is applied at least partly between the projections in said at least one substrate zone. Moreover there is provided a method for the analysis of a sample. The device and method provide for instance improved control of the dissolution of a substance.

18 Claims, 3 Drawing Sheets

(56) References Cited

U.S. PATENT DOCUMENTS

| | | | |
|---|---|---|---|
| 2005/0244985 A1* | 11/2005 | Freitag et al. | 436/514 |
| 2006/0000772 A1* | 1/2006 | Sano et al. | 210/635 |
| 2006/0239859 A1* | 10/2006 | Ohman et al. | 422/100 |
| 2006/0285996 A1* | 12/2006 | Ohman et al. | 422/57 |
| 2007/0266777 A1* | 11/2007 | Bergman et al. | 73/61.41 |
| 2008/0176272 A1* | 7/2008 | Bergman et al. | 435/29 |
| 2009/0111197 A1* | 4/2009 | Khan et al. | 436/536 |
| 2009/0208920 A1* | 8/2009 | Ohman et al. | 435/2 |

FOREIGN PATENT DOCUMENTS

| | | |
|---|---|---|
| WO | WO-03/103835 A1 | 12/2003 |
| WO | WO-2005/089082 A2 | 9/2005 |
| WO | WO-05/112054 A1 | 11/2005 |
| WO | WO-2005/118139 A1 | 12/2005 |
| WO | WO-2006/137785 A1 | 12/2006 |
| WO | WO-2007/012975 A1 | 2/2007 |

* cited by examiner

ASSAY DEVICE AND METHOD

The present application claims the benefit of U.S. Provisional Application Ser. No. 61/061,983. filed on Jun. 16, 2008. the contents of which are hereby incorporated by reference, in its entirety.

TECHNICAL FIELD

The present invention concerns an assay device for the analysis of a liquid sample.

BACKGROUND

Quick, reliable, and cost effective analytical and diagnostic devices for instance devices for use in point of care are desirable.

In many assays, detection conjugate and possibly further reagents are predispensed or integrated in the device, setting aside the need for separate addition of reagents by the user.

A common type of disposable assay device comprises a zone for receiving the sample, a reaction zone, and optionally a transport or incubation zone connecting the receiving and reaction zone, respectively. These assay devices are known as immunochromatography assay devices or simply referred to as strip tests.

PCT/SE03/00919 relates to a micro fluidic system comprising a substrate and provided on said substrate there is at least one flow path comprising a plurality of micro posts protruding upwards from said substrate, the spacing between the micro posts being small enough to induce a capillary action in a liquid sample applied, so as to force said liquid to move.

PCT/SE2005/000429 shows a device and method for the separation of a component in a liquid sample prior to the detection of an analyte in said sample, wherein a sample is added to a receiving zone on a substrate, said substrate further optionally comprising a reaction zone, a transport or incubation zone connecting the receiving and reaction zone, respectively, forming a flow path on a substrate, wherein said substrate is a non-porous substrate, and at least part of said flow path consists of areas of projections substantially vertical to the surface of said substrate, and having a height, diameter and reciprocal spacing such, that lateral capillary flow of said liquid sample in said zone is achieved, and where means for separation are provided adjacent to the zone for receiving the sample.

PCT/SE2005/000787 concerns a device for handling liquid samples, comprising a flow path with at least one zone for receiving the sample, and a transport or incubation zone, said zones connected by or comprising a zone having projections substantially vertical to its surface, said device provided with a sink with a capacity of receiving said liquid sample, said sink comprising a zone having projections substantially vertical to its surface, and said sink being adapted to respond to an external influence regulating its capacity to receive said liquid sample.

PCT/SE2006/000745 relates to an absorbing zone for establishing and/or maintaining fluid transport through or along said at least one fluid passage is manufactured on the basis of a non-porous substrate, having projections substantially perpendicular to said surface, and said projections having a height, diameter and a distance or distances between the projections such, that lateral capillary flow of said fluid in said zone is achieved.

Although the assay devices comprising projections according to the prior art are working satisfactory there is still room for a further improvement regarding for instance the control of the dissolution of a substance that is applied on the device.

SUMMARY OF THE INVENTION

One object of the present invention is to provide a device where the control of the dissolution of a predispensed substance is further improved. There is made available an analysis device for the analysis of a liquid sample, said device comprising a substrate, said substrate at least partly having projections substantially vertical to the surface of said substrate, and having a height (H1), diameter (D1) and center-to-center distance (x1, y1) such, that lateral capillary flow of said liquid sample is achieved, wherein said substrate comprises at least one substrate zone comprising projections substantially vertical to the surface of said substrate, and having a height (H2), diameter (D2) and center-to-center distance (x2, y2), such, that lateral capillary flow of said liquid sample is achieved and wherein at least one substance is applied at least partly between the projections in said at least one substrate zone.

Further aspects and embodiments of the present invention are defined in the appended claims which are incorporated herein by reference.

SHORT DESCRIPTION OF THE DRAWINGS

The invention will be described in closer detail in the following description, examples, and attached drawings, in which.

DEFINITIONS

Before the present device and method is described, it is to be understood that this invention is not limited to the particular configurations, method steps, and materials disclosed herein as such configurations, steps and materials may vary somewhat. It is also to be understood that the terminology employed herein is used for the purpose of describing particular embodiments only and is not intended to be limiting since the scope of the present invention will be limited only by the appended claims and equivalents thereof. It must also be noted that, as used in this specification and the appended claims, the singular forms "a", "an", and "the" include plural referents unless the context clearly dictates otherwise. Thus, for example, reference to a reaction mixture containing "an antibody" includes a mixture of two or more antibodies.

The term "about" when used in the context of numeric values denotes an interval of accuracy, familiar and acceptable to a person skilled in the art. Said interval can be ±10% or preferably ±5%.

In describing and claiming the device and method, the following terminology will be used in accordance with the definitions set out herein.

As used throughout the claims and the description the term "analysis" means the process in which at least one analyte is determined.

As used throughout the claims and the description the term "analysis device" means device by the aid of which an analysis can be performed.

As used throughout the claims and the description the term "analyte" means a substance or chemical or biological constituent of which one or more properties are determined in an analytical procedure. An analyte or a component itself can often not be measured, but a measurable property of the analyte can. For instance, it is possible measure the concentration of an analyte.

As used throughout the claims and the description the term "capillary flow" means flow induced mainly by capillary force.

As used throughout the claims and the description the term "casing" means an element enclosing a part of or the entire substrate.

As used throughout the claims and the description the term "center-to-center distance" means the distance between adjacent projections, measured from the center of a projection to the center of an adjacent projection. For a planar substrate the center-to-center distance is measured both in the x direction and in the y direction, in an orthogonal coordinate system in the substrate plane.

As used throughout the claims and the description the term "center of a projection" means the center of gravity for an infinitesimal thin slice of the projection taken on half of the height of the projection in a plane parallel to the surface of the substrate. For curved substrates the plane is parallel to the surface of the substrate in a sufficiently small surrounding around the projection.

As used throughout the claims and the description the term "connecting zone" means a zone which establishes fluid connection between at least two other zones.

As used throughout the claims and the description the term "detectable group" means any arrangement of molecules or atoms that can be detected when present on a substrate.

As used throughout the claims and the description the term "fluid connection" means a connection in which a fluid can be transported.

As used throughout the claims and the description the term "sample" means a mixture or a solution to be analyzed.

As used throughout the claims and the description the term "substance" means any pure chemical or biological entity or any mixture or solution comprising at least one chemical or biological entity.

DETAILED DESCRIPTION

In a first aspect there is provided an analysis device for the analysis of a liquid sample, said device comprising a substrate, said substrate at least partly having projections substantially vertical to the surface of said substrate, and having a height, diameter and center-to-center distance such, that lateral capillary flow of said liquid sample is achieved, and said substrate comprises at least one substrate zone comprising projections substantially vertical to the surface of said substrate, and having a height (H2), diameter (D2) and center-to-center distance (x2, y2), such, that lateral capillary flow of said liquid sample is achieved and wherein at least one substance is applied at least partly between the projections in said at least one substrate zone.

When a liquid sample is added to the substrate a flow is created by capillary forces due to the projections on the surface, where the projections have a height (H1), diameter (D1) and center-to-center distance (x1, y1). There is also at least one zone which is covered with projections, where the projections have a different height (H2), diameter (D2) or center-to-center distance (x2, y2), compared to the other projections on the substrate with a height (H1), diameter (D1) and center-to-center distance (x1, y1). In one embodiment at least one of the properties height, diameter and center-to-center distance is different between the zones. In another embodiment the height, diameter and center-to-center distance are different. In a further embodiment the diameter and center-to-center distance are different. In one embodiment H1 and H2 are different. In one embodiment D1 and D2 are different. In one embodiment x1 and x2 are different. In one embodiment y1 and y2 are different. In further embodiments several of the parameters H, D, x and y are different. In one embodiment all parameters H, D, x and y are the same for at least two zones of the substance. In one embodiment all parameters H, D, x and y are the same for the entire device.

At least one substance is applied between projections on the substrate. In one embodiment the substance is applied entirely within the at least one substrate zone. In an alternative embodiment at least one substance is applied both in the at least one substrate zone and outside the at least one substrate zone.

In one embodiment the projections in the substrate zone have a different height (H2), diameter (D2) or center-to-center distance (x2, y2) so that the substrate zone has an appearance which is different from the surrounding. This is an advantage when the device is manufactures since the zone where a substance is to be applied can easily be identified by a human eye or by an automated device.

In one embodiment the projections in the substrate zone have a different height (H2), diameter (D2) or center-to-center distance (x2, y2) so that the substrate zone exerts a different capillary force on a substance in solution compared to the surrounding. This facilitates the addition of a substance in a solution or a suspension. In one embodiment the capillary force exerted by the substrate zone is higher than for the surrounding and thus a substance in a solution or a suspension can easier be applied to the substrate zone only. The substance to be applied is in one embodiment dissolved or suspended in a solvent and applied to the substrate. The solvent is in one embodiment evaporated and the substance is thus left on the substrate. This has the advantage to create a well defined area in which the substance is applied. The boundaries of the applied substance are sharp.

In one embodiment the substance is applied in a volume between the projections of the substrate zone. When the substance is applied to the substrate the capillary force exerted from the projections of the substrate zone in one embodiment causes the substance in solution or suspension to fill out essentially the entire volume between the projections of the substrate zone.

In one embodiment the projections of the substrate zone(s) have a height (H2), diameter (D2) and center-to-center distance (x2, y2) such that the capillary force exerted by the projections facilitate addition of said substance(s) to the substrate zone(s).

In one embodiment the substance is an essentially pure substance. In another embodiment the at least one substance is a mixture of two or more substances.

Examples of substances which can be applied on the substrate include but are not limited to antibodies, DNA, RNA, aptamers, antibodies directed to specific analytes in a sample, fragmented antibodies, antibody fragments, synthetic binders, chemical binders, receptors, ligands, affibodies, cells, organelles, polypeptides, peptides, enzymes, monoclonal antibodies, polyclonal antibodies, phage display proteins, IgG immunoglobulins, chemical ligands, and combinations thereof.

In one embodiment the substance to be applied to the substrate comprises at least one further additive. Examples of further additives include but are not limited to sugars, polymers, detergents, surface active agents, cationic surface active agents, non-ionic surface active agents, anionic surface active agents, salts, and lipids or any combination thereof.

In one embodiment there is added at least one further substance to the substrate, where that substance is at least one substance selected from a sugar, a polymer, a detergent, a surface active agent, a cationic surface active agent, a non-ionic surface active agent, an anionic surface active agent, a salt, and a lipid.

In one embodiment the substrate further comprises in sequence; at least one sample addition zone, at least one connecting zone, and at least one receiving zone in fluid connection, wherein said connecting zone comprises at least one reaction zone, and wherein said at least one substrate zone is between said sample addition zone and said reaction zone. In one embodiment at least a part of the connecting zone is covered by projections such that a lateral capillary flow is achieved.

In one embodiment at least one zone is surrounded by an area where at least one of the height (H), diameter (D) and center-to-center distance (x, y) of the projections is different so that the surrounding projections exert a lower capillary force on the sample liquid then the zone. In one embodiment said zone is at least one zone selected from the reaction zone and the substrate zone. In one embodiment said zone is the substrate zone. In one embodiment the center-to-center distance in an area surrounding a zone is larger compared to within the zone.

Figure 6:
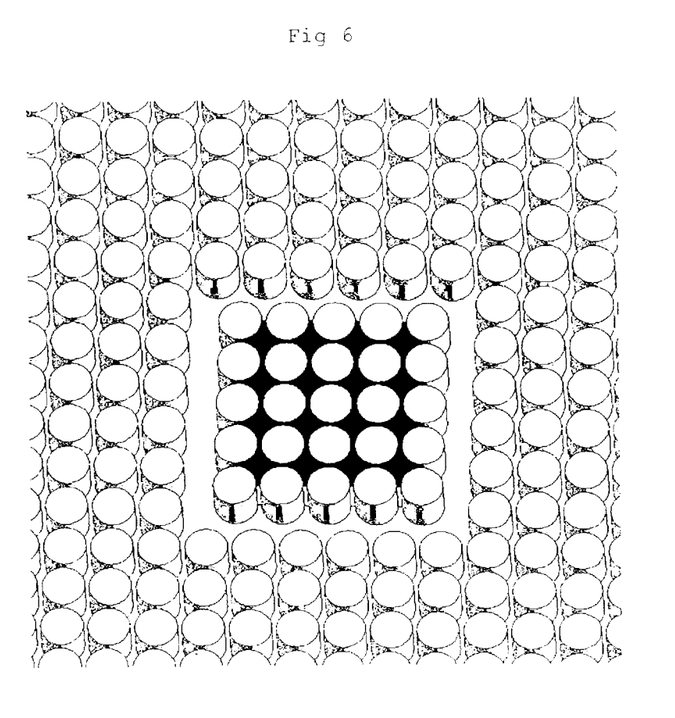
FIG. 6 shows an embodiment with a substrate zone where a substance has been applied between the projections in the substrate zone. There is an area surrounding the substrate zone where there are no projections.

In one embodiment there is an area without any projections surrounding at least one of the substrate zone and the reaction zone. In FIG. 6 there is depicted one embodiment where an area without projections is surrounding a substrate zone. In one embodiment the surrounding area without projections is from 15 to 100 μm wide. In another embodiment the surrounding area without projections is from 20 to 40 μm wide. In a further embodiment the surrounding area without projections is from 25 to 35 μm wide. The width depends on the viscosity of the substrate which is added to the substrate zone and on the hydrophilicity of the surface surrounding the substrate zone.

Advantages of a zone with a surrounding area with different properties include that it is possible to apply a substance to the zone without the substance flowing out of the zone. Thus it is possible to apply a substance to a zone in a reproducible and well defined manner.

In one embodiment the entire connecting zone is covered by projections such that a lateral capillary flow is achieved. In one embodiment at least a part of the sample addition zone, the connecting zone and the receiving zone are covered by projections such that a lateral capillary flow is achieved. In another embodiment the entire sample addition zone, connecting zone and receiving zone are covered by projections such that a lateral capillary flow is achieved.

In one embodiment the analysis device and the substrate is such that it is possible to add a sample to the sample addition zone. Due to capillary flow induced by the projections a lateral flow is created and at least a part of the sample reaches at least one substrate zone on the substrate where there are projections with a height (H2), diameter (D2) and center-to-center distance (x2, y2). In one embodiment the substance applied in the at least one substrate zone and/or near the at least one substrate zone is gradually dissolved by the sample flowing by the at least one substrate zone. The liquid sample thereafter reaches the reaction zone. In one embodiment a measurement is made in the reaction zone. Examples of measurement techniques include but are not limited to detection of fluorescence, and chemiluminescence. A person skilled in the art realizes that also other detection principles can be used such as absorption of light optionally at several different wavelengths, and detection of emitted light. In one embodiment the sample continues to a receiving zone, which receives the liquid sample. The flow continues until there is no more liquid sample or until the receiving zone is full of sample liquid.

In one embodiment there is a surplus of sample liquid. In one embodiment a part of the surplus of sample liquid is used so that when all of the substance has been dissolved the reaction zone and other parts of the device is washed so that free or loosely bound substance is washed away.

In one embodiment there are several receiving zones.

The at least one substance, which is applied to the at least one substrate zone, is in one embodiment applied to the substrate surface. In one embodiment the substance is applied between the projections. In one embodiment the thickness of the applied substance in a dried state is essentially corresponding to the height of the projections. In an alternative embodiment the thickness of the applied substance in a dried state is lower than the height of the projections. In one embodiment the thickness of the applied substance in a dried state is higher than the projections.

In one embodiment the at least one substance is applied in a volume between the projections in said at least one substrate zone, so that the substance in a dried state fills a volume up to a level at half of the height (H2) of the projections.

In an alternative embodiment the at least one substance is applied in a volume between the projections in said at least one substrate zone, so that the substance in a dried state fills a volume up to essentially the same height (H2) as the projections.

In a further embodiment the at least one substance is applied in a volume between said projections in said at least one substrate zone, so that the substance in a dried state fills a volume up to a level so that there is essentially no liquid flow on top of said at least one substance.

In one embodiment the volume between the projections of the substrate zone is adjusted so that the amount of substance which is to be applied fills up to the desired level in a dried state.

In one embodiment the substance is applied in a solution and is dried so that a solvent is evaporated. In one embodiment the solvent is water. When the solvent has evaporated the remaining substance is called the substance in a dried state.

In embodiments where the there is no flow or essentially no flow of liquid on top of the applied substance, the dissolution of the applied substance occurs from the sides and not from the top. This gives a controlled dissolution. The dissolution occurs during a prolonged time and in a more controlled manner compared to an embodiment where the liquid sample also flows over the applied substance.

In one embodiment no liquid flows on top of the applied substance. In an alternative embodiment only a minor part of the liquid flows on top of the applied substance, examples of such a part of the liquid include but are not limited to 0.1 wt %, 1 wt %, 5 wt %, and 10 wt %. In one embodiment less than 1 wt % of the liquid flows on top of the applied substance. In another embodiment less than 10 wt % of the liquid flows on top of the applied substance.

By adjusting the diameter and center-to-center distance of the projections for instance in an embodiment where essentially no liquid flows over the applied substance, it is possible to control the dissolution of the applied substance in the liquid.

In one embodiment all components of the applied substance are dissolved by the liquid sample. In an alternative embodiment not all applied substances are dissolved by the liquid sample.

By adjusting the height, diameter and center-to-center distance of the projections in the zone where a substance has been applied and outside the zone where a substance has been applied it is possible to control the lateral capillary flow so that a desired dissolution of the applied substance occurs at a desired rate.

In one embodiment the heights ($H1$, $H2$), diameters ($D1$, $D2$) and center-to-center distances ($x1$, $x2$, $y1$, $y2$) are adapted so that said at least one substance is gradually dissolved in a flow of a liquid flowing by said substrate zone.

The invention is not limited to two different heights, diameters and center-to-center distances of the projections. There are provided embodiments with further zones, where each zone has a height, diameter, and center-to-center distance, where at least one of the parameters is different compared to the other zones.

There is provided an embodiment where the analysis device comprises at least one additional zone n, where each additional zone n comprises projections substantially vertical to the surface of said substrate, with a height ($H_n$), diameter ($D_n$) and center-to-center distance ($x_n$, $y_n$), such that lateral capillary flow is created. There is provided a substrate having n distinct zones, each zone comprising projections having a height ($H_n$), diameter ($D_n$) and center-to-center distance ($x_n$, $y_n$), where n is a natural number. n=1, 2, 3, 4, 5, 6 . . .

In one embodiment there is at least one substance applied in at least one of the n zones.

In one embodiment there is a substrate zone comprising projections substantially vertical to the surface of said substrate, and having a height, diameter and center-to-center distance, such, that lateral capillary flow of said liquid sample is achieved, where the height, diameter and center-to-center distance in the substrate zone is different from outside of the substrate zone. In one embodiment the height, diameter and center-to-center distance of the projections vary within the substrate zone.

In one embodiment there are at least two zones comprising an applied substance, which zones have the shape of concentric circles. In one embodiment the outer part comprises at least one applied substance and the inner part comprises at least one another applied substance. First the outer substance is dissolved and then the inner substance is dissolved. Thereby further possibilities to control the dissolution are provided. There is also provided possibility to dissolve several substance in sequence or together. In one embodiment there is provided the possibility to dissolve more than one substance in sequence. In other embodiments also other shapes of the different zones with applied substances are provided. In one embodiment there is at least one zone which first comes into contact with the sample liquid and when a fraction of or all of the substance in that zone has dissolved the sample liquid comes into contact with another zone comprising a different substance. Thereby it is possible to start the dissolution of a substance in the sample liquid after a certain period of time.

Thus there is provided a method wherein the at least one zone first comes into contact with liquid sample and when at least a part of applied substance in said zone has dissolved, the liquid sample comes into contact with another zone comprising another applied substance.

In one embodiment there are two different zones, where each zone comprises a distinct substance.

In one embodiment a part of the liquid sample passes the zone(s) where a substance has been applied at such a distance that essentially no substance is dissolved, and another part passes near the zone where a substance has been applied so that the substance dissolves in the liquid. Thus there is a provided an embodiment where a part of the liquid stream flowing through the device comprises a major part of dissolved substance and another part comprises little or no dissolved substance. Examples of a major part of the dissolved substance include but are not limited to 75 wt %, 90 wt %, 95 wt %, 99 wt %, and 99.9 wt %.

It is possible to control the height, diameter and center-to-center distance of the projections inside and outside of the zone where the substance to be dissolved is applied. In that way it is possible to control the fraction of the liquid sample that flows by the zone where the substance is dissolved. By controlling the rate at which the substance dissolves when the liquid sample flows by, it is possible to control the concentration of the dissolved substance.

Figure 1:
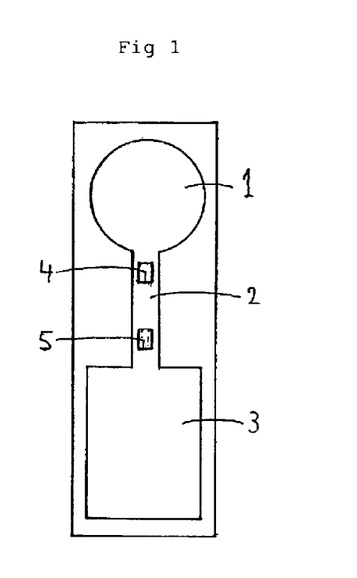
FIG. 1 shows an embodiment from above, where there is shown one sample addition zone 1, one connecting zone 2, one receiving zone 3 as well as a substrate zone 4 comprising projections with a diameter which is larger than the diameter for the surrounding projections. There is also a reaction zone 5. Between projections in the substrate zone 4 there is an applied substance.
Figure 2:
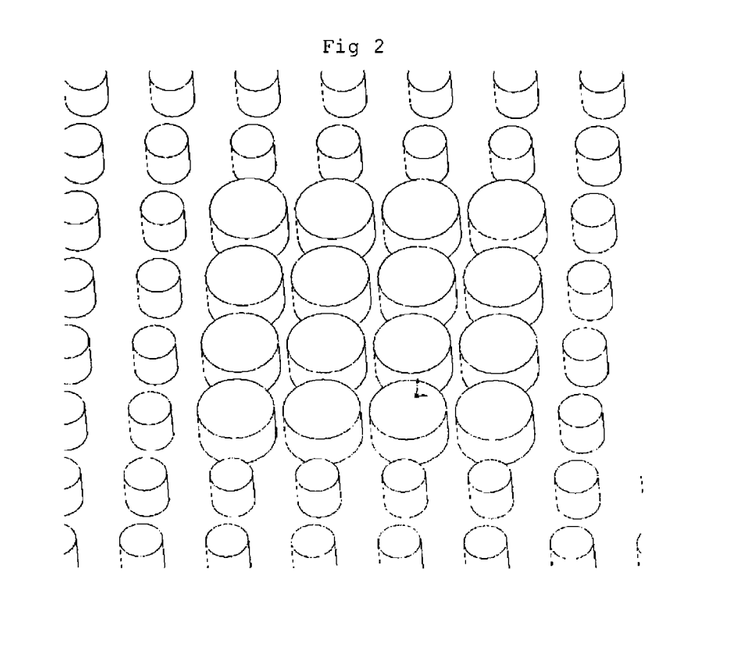
FIG. 2 shows an embodiment where there is a substrate zone comprising projections with a diameter D2, which is larger than the diameter D1 for the surrounding projections.
Figure 3:
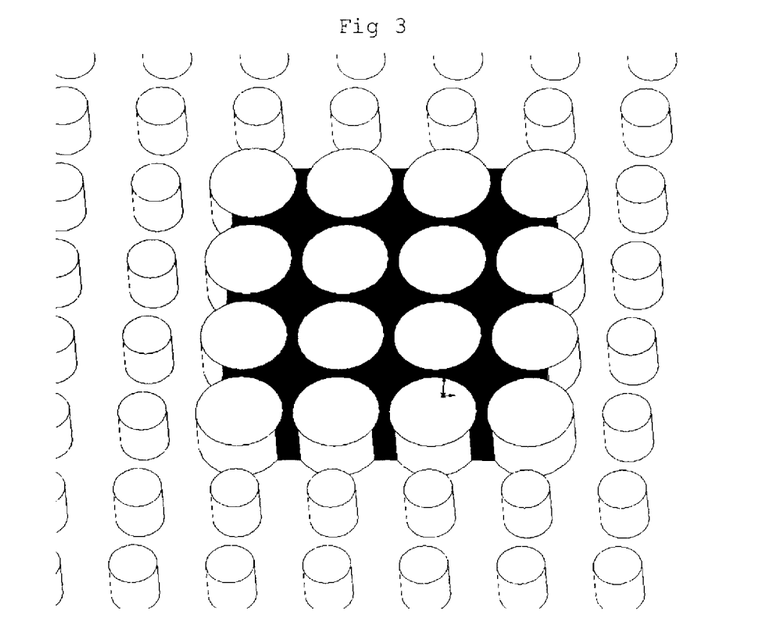
FIG. 3 shows an embodiment as in FIG. 2 where a substance has been applied in the substrate zone.
Figure 4:
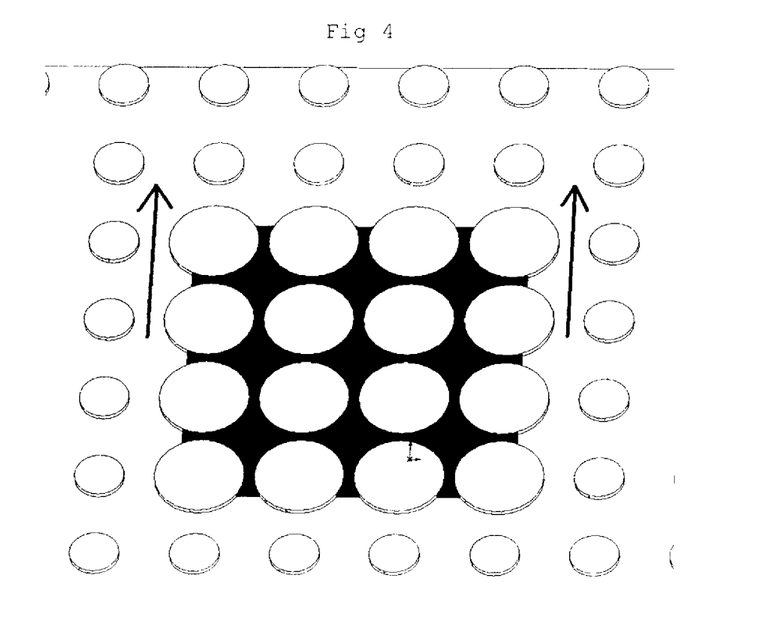
FIG. 4 shows an embodiment with a substrate zone comprising projections with a larger diameter than the surrounding projections. A substance has been applied between the projections in the substrate zone. The arrows indicate the direction of a flow of liquid.
Figure 5:
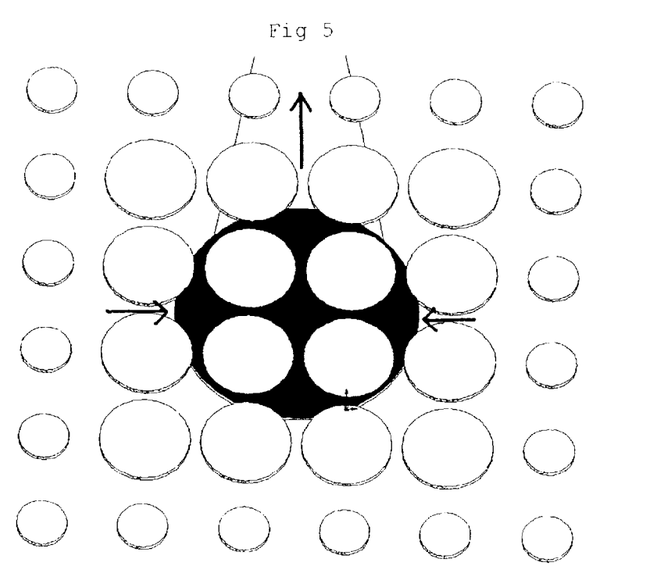
FIG. 5 shows the same embodiment as in FIG. 4 after a period of time. The arrows indicate that a part of the substance has dissolved in the liquid and is brought in the direction of the flow.

If a larger fraction of liquid sample passes outside the zone where the substance is dissolved at a high flow, the result is that downstream of the zone where the sample is applied; there is a rather narrow concentrated flow of dissolved substance. On the other hand, if a smaller fraction of liquid sample passes the zone where the substance is dissolved the result is that downstream of the zone where the sample is applied; there is a broader trace of dissolve substance. The trace of dissolved substance is shown in FIG. 5 as a grey area.

In one embodiment the result is detected in the middle of the trace of dissolved substance downstream of the zone where the substance is applied. In one embodiment the result of the analysis is read in the reaction zone, downstream of the zone where the substance is applied.

The shape of the zone where the substance is applied is in one embodiment adapted to control the dissolution rate and/or how the dissolved substance is distributed in the flow of liquid sample.

Examples of shapes include but are not limited to a triangle, a square, a rectangle, a parallelogram, a rhombus, a trapezoid, a quadrilateral, a polygon, a circle, and an oval.

Also truncated shapes are encompassed, including but not limited to a half circle, a half oval, a half polygon, and a circle segment.

Further shapes include all possible combinations of shapes including but not limited to a triangle and a square, a triangle and a rectangle, a trapezoid and a rectangle, a half circle and a rectangle and so on.

In one embodiment the shape of the zone where the substance is applied is triangular with one of the corners pointing in the direction from where the flow of sample liquid comes.

In one embodiment the shape of the zone where the substance is applied is an isosceles trapezoid.

In one embodiment the shape of the zone where the substance is applied is an isosceles trapezoid combined with a rectangle.

In one embodiment the shape of the zone where the substance is applied is an isosceles trapezoid combined with a rectangle, with the narrower zone pointing towards the direction from where the flow of sample liquid comes.

In one embodiment the shape of the zone where is substance is applied and the height, diameter and center-to-center distance of the projections are adapted so that the concentration of the dissolved substance is greater towards the middle of the substrate.

In one embodiment the analysis device further comprises a lid. Preferably the lid has at least one opening or an aperture for the addition of a liquid sample. In one embodiment there is an opening or a window allowing a measurement result to be read from the analysis device. If a lid is used the lid is not in capillary contact with the projections on the substrate. The lid does not take part in creating any capillary forces.

In one embodiment the analysis device comprises a casing. In one embodiment the casing encloses the entire or a part of the analysis substrate. Preferably the case has at least one opening or an aperture for the addition of a liquid sample. In one embodiment there is an opening or a window allowing a measurement result to be read from the analysis device.

In one embodiment the applied substance comprises a detection conjugate. In one embodiment the detection conjugate comprises at least one element selected from an antibody, DNA, RNA, an aptamer, a fragmented antibody, an antibody fragment, a synthetic binder, a chemical binder, a receptor, a ligand, an affibody, a cell, an organelle, a polypeptide, a peptide, an enzyme, a monoclonal antibody, a polyclonal antibody, a phage display protein, an IgG immunoglobulin, a chemical ligand. In one embodiment the detection conjugate comprises more than one antibody. In one embodiment at least one of the molecules in the applied substance comprises a detectable group, which allows detection for instance in the reaction zone. The detection conjugate facilitates detection of an antigen bound to the conjugate. In one embodiment the detection conjugate comprises a fluorescent molecule. In one embodiment fluorescence from the detection conjugate is measured.

In one embodiment at least one selected from an antibody, DNA, RNA, an aptamer, a fragmented antibody, an antibody fragment, a synthetic binder, a chemical binder, a receptor, a ligand, an affibody, a cell, an organelle, a polypeptide, a peptide, an enzyme, a monoclonal antibody, a polyclonal antibody, a phage display protein, an IgG immunoglobulin, and a chemical ligand, is bound to the substrate downstream of the applied substance. Such an antibody or aptamer is able to bind to the complex between an antibody and an antigen or to a free antigen. In one embodiment an antibody or an aptamer bound to the reaction zone is able to bind to the complex between an antibody and an antigen or to a free antigen. In one embodiment fluorescence from the detection conjugate in the reaction zone is measured.

In a second aspect there is provided a method for the analysis of a sample comprising the steps of: a) addition of a liquid sample on at least one spot on a substrate, and b) performing at least one measurement on the substrate, wherein an analysis device as described herein is used.

In one embodiment the substrate is first wetted by sample liquid comprising essentially no dissolved substance and then is brought into contact with liquid sample comprising dissolved substance. The first wetting by the liquid sample is achieved by a delay of the dissolution of the substance applied to the substrate. The sample liquid that flows first comprises essentially no dissolved substance, such as but not limited to less than 0.001 wt %, 0.01 wt %, 0.1 wt % or 1 wt %. When the liquid sample comes into contact with the substance, the dissolution process starts and the level of dissolved substance gradually increases.

In one embodiment there are molecules bound to the substrate which are first hydrated by the liquid sample, where the liquid sample is essentially without any dissolved substance. In one embodiment such molecules are antibodies. One advantage of such a pre-hydration is that the antibodies or molecules become more active. This first hydration is called a pre wetting. In one embodiment a substantial part of the substance(s) applied to the substrate is dissolved and transported across the reaction zone after a steady lateral flow has been established by the capillary force from the receiving zone. A substantial part of the substance(s) applied to the substrate is in this case more than 75 wt %, preferably more than 90 wt %, more preferably more than 95 wt % and most preferably more than 99 wt %.

In one embodiment the sample is added to a sample addition zone, the sample flows through a connecting zone to a receiving zone. The receiving zone has a capacity to receive the sample liquid and has a large surplus of capillary force. The capillary force of the receiving zone is in one embodiment such that a steady and even lateral flow of sample liquid is created. The capillary force of the receiving zone acts like a pump and receives the sample liquid at a steady rate. Before the added sample liquid has reached the receiving zone the lateral capillary flow is not always even and steady.

It is one advantage that a substantial part of the applied substance is not dissolved until there is a steady lateral flow, i.e. when the liquid sample has reached the receiving zone. In that way the dissolution of the substance occurs at a more controlled way due to the steady and even flow of sample liquid.

In one embodiment the substrate comprises a receiving zone with the capacity to receive liquid sample, and wherein more than 95 wt % of the applied substance is not dissolved until any part of the liquid sample has reached the receiving zone. In an alternative embodiment more than 90 wt %, preferably 94 wt %, more preferably 99 wt % and most preferably 99.9 wt % of the applied substance is not dissolved until any part of the liquid sample has reached the receiving zone. This implies that at most 10 wt %, preferably 6 wt %, more preferably 1 wt % and most preferably 0.1 wt % of the applied substance is dissolved until any part of the liquid sample reaches the receiving zone.

Further advantages include that there is provided a possibility of increased control of the flow. There is also provided the possibility of dissolution during a steady lateral flow. It is possible to control the start and stop of dissolution of a substance. There is a possibility to provide a wash of the reaction zone after the dissolved substance(s) has passed. It is possible to obtain an even dissolution of the reagent over time. There is the possibility to ensure that the dissolved substance is spatially homogenously distributed. There is also provided the possibility to control the spatial distribution of the dissolved substance. It is possible to ensure that all substance is dissolved in the sample. A major portion of the sample is contacted with the substance.

EXAMPLES

Example 1

A substrate with dimensions 25×75 mm was made by injection molding of a cyclo olefin polymer (COP). The substrate hade a sample addition zone, a substrate zone, a connecting zone, a reaction zone, and a receiving zone. On the substrate there were projections with height 70 μm and diameter 50 μm. The distance between the projections were 15 μm in the sample addition zone, the substrate zone, the connecting zone, and the reaction zone. A distance between the projections of 15 μm and a diameter of 50 μm corresponds to a center-to-center distance of 65 μm between the projections in both x- and y-direction. The substance zone was surrounded by a gap where the distance between the projections was 30 μm.

It was possible to apply detection conjugate to the substance zone so that the detection conjugate did not move out of the substrate zone. The application of the detection conjugate was reproducible during several applications. The detection conjugate was applied so that the height of the dried detection conjugate was at about the same level as the top of the projections in the substance zone.

A detection conjugate comprising antibodies against N-terminal pro-brain natriuretic peptide (NT-proBNP) was used.

Separated whole blood was added to the sample addition zone and the detection conjugate dissolved gradually in the liquid sample. The trace of dissolved detection conjugate was continuous and the dissolution time could be controlled. The experiment was repeated six times and the dissolution time of the detection conjugate was 6 minutes and 8 seconds, whereby the coefficient of variation was 3%.

The total assay time was 19 minutes and 19 seconds with a coefficient of variation of 5% (six repeated experiments).

The result of the analysis was read by using an optical reader.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto.

What we claim:

1. An analysis device for the analysis of a liquid sample, said device comprising:
    a substrate, said substrate including:
        a sample addition zone;
        a receiving zone downstream of the sample addition zone and along a defined fluid flow path,
        a connecting zone bridging the sample addition zone and the receiving zone, each of the sample addition zone, receiving zone and connecting zone being along the defined fluid flow path and having projections substantially vertical to the surface of said substrate, said projections having a first height, first diameter and first center-to-center distance such that lateral capillary flow of said liquid sample is achieved when sample is dispensed onto the sample addition zone of said device; and
        at least one substrate zone disposed between said sample addition zone and said receiving zone and entirely surrounded within the connecting zone, said at least one substrate zone comprising a plurality of projections substantially vertical to the surface of said substrate, and having at least one of a second height, second diameter and second center-to-center distance, such that lateral capillary flow of said liquid sample is achieved and further having at least one chemical substance applied at least partly between the projections in said at least one substrate zone prior to dispensing of said liquid sample onto the sample addition zone of said analysis device, wherein the projections of the at least one substrate zone(s) produce increased capillary force on a liquid as compared to the surrounding zones in order to confine the applied chemical substance within the at least one substrate zone prior to application of the liquid sample.

2. The analysis device according to claim 1, wherein said substrate further comprises in sequence: at least one sample addition zone, at least one connecting zone, and at least one receiving zone in fluid connection, wherein said at least one connecting zone comprises at least one reaction zone, and wherein said at least one substrate zone is disposed between said at least one sample addition zone and said at least one reaction zone.

3. The analysis device according to claim 1, wherein said at least one substrate zone is surrounded by an area where at least one of the height, diameter and center-to-center distance of the projections exert a lower capillary force on the liquid than the substrate zone.

4. The analysis device according to claim 1, wherein an area without any projections surrounds the at least one substrate zone.

5. The analysis device according to claim 2, wherein an area without any projections surrounds the at least one reaction zone.

6. The analysis device according to claim 1, wherein said at least one chemical substance is applied in a volume between the projections in said at least one substrate zone, so that the substance in a dried state fills a volume up to essentially the same height as the projections and in which lateral capillary flow occurs around said substrate zone.

7. The analysis device according to claim 1, wherein said at least one chemical substance is applied in a volume between said projections in said at least one substrate zone, so that the substance in a dried state fills a volume up to a level so that there is essentially no liquid flow on top of said at least one substance, and in which lateral capillary flow occurs around said substrate zone.

8. The analysis device according to claim 1, wherein the heights, diameters and center-to-center distances of said projections are adapted so that said at least one chemical substance is gradually dissolved in a flow of liquid flowing by said at least one substrate zone.

9. The analysis device according to claim 1, further comprising at least one additional zone, said at least one additional zone comprising projections on substantially vertical to the surface of said substrate, each projection having a height, diameter and center-to-center distance between projections, and wherein said at least one chemical substance is applied in at least one said additional zone.

10. The analysis device according to claim 1, wherein the at least one substrate zone has a shape selected from the group consisting of a triangle, a square, a rectangle, a parallelogram, a rhombus, a trapezoid, a quadrilateral, a polygon, a circle, an oval, a half circle, a half oval, a half polygon, and a circle segment.

11. The analysis device according to claim 1, further comprising a casing.

12. A method for the analysis of a sample comprising the steps of:
    a. addition of a liquid sample on at least one spot on a substrate;
    b. performing at least one measurement on the substrate, wherein an analysis device according to claim 1 is used.

13. The method according to claim 12, wherein the substrate first is wetted by sample liquid comprising essentially no dissolved substance and then is brought into contact with liquid sample comprising dissolved substance.

14. The method according to claim 12, wherein the substrate comprises a receiving zone with the capacity to receive liquid sample, and wherein more than 95 wt % of the applied substance is not dissolved until any part of the liquid sample has reached the receiving zone.

15. The method according to claim 12, wherein the at least one zone first comes into contact with liquid sample and when at least a part of applied substance in said zone has dissolved, the liquid sample comes into contact with another zone comprising another applied substance.

16. An analysis device for the analysis of a liquid sample, said device comprising:
  a substrate including:
    a sample addition zone;
    a receiving zone;
    a connecting zone disposed between the sample addition zone and the receiving zone, each of the zones having projections substantially vertical to the surface of the substrate said projections having a height, diameter and center-to-center distance such that lateral capillary flow of said liquid sample is achieved when sample is dispensed onto said sample addition zone of said device along a fluid flow path; and
  at least one substrate zone disposed between said sample addition zone and said receiving zone and entirely contained within the connecting zone, said at least one substrate zone comprising a plurality of said projections such that lateral capillary flow of said liquid sample is achieved and further having at least one chemical substance applied at least partly between the projections in said at least one substrate zone prior to dispensing of said liquid sample onto the sample addition zone of said analysis device wherein an area without any projections entirely surrounds the periphery of the at least one substrate zone.

17. The analysis device according to claim 16, wherein the projections in the at least one substrate zone have at least one of a different height, diameter and center-to-center distance such that the at least one substrate zone has an appearance which is different from the surrounding zones.

18. The analysis device according to claim 16, wherein the projections in the at least one substrate zone have the same height, diameter and center-to-center distance as those in the surrounding zones.

* * * * *